(12) United States Patent
Onishi et al.

(10) Patent No.: US 6,639,094 B2
(45) Date of Patent: Oct. 28, 2003

(54) PROCESS FOR PRODUCING α-AMINOKETONE DERIVATIVES

(75) Inventors: Tomoyuki Onishi, Kawasaki (JP); Takashi Nakano, Kawasaki (JP); Naoko Hirose, Kawasaki (JP); Takayoshi Torii, Kawasaki (JP); Masakazu Nakazawa, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 15 days.

(21) Appl. No.: 09/949,614

(22) Filed: Sep. 12, 1999

(65) Prior Publication Data

US 2002/0026081 A1 Feb. 28, 2002

Related U.S. Application Data

(63) Continuation of application No. PCT/JP00/01498, filed on Mar. 13, 2000.

(30) Foreign Application Priority Data

Mar. 12, 1999 (JP) .............................. 11-066712

(51) Int. Cl.⁷ ............................................. C07C 261/00
(52) U.S. Cl. .............................. 560/24; 560/35; 560/38; 560/157; 560/161; 560/162; 562/422; 568/805; 568/30; 568/307
(58) Field of Search ................................. 568/305, 306, 568/307; 562/422; 860/24, 35, 38, 157, 161, 162

(56) References Cited

U.S. PATENT DOCUMENTS 6,020,518 A * 2/2000 Matsumoto et al.

FOREIGN PATENT DOCUMENTS

| EP | 0 930 292 | 7/1999 |
|---|---|---|
| EP | 1 078 919 | 2/2001 |
| WO | 98/07687 | 2/1998 |
| WO | 00/5513 | 9/2000 |
| WO | WO 00/53575 | 9/2000 |

OTHER PUBLICATIONS

Cathy Bacquet, et al., C. R. Acad. Sc. Paris, vol. 278, pp. 929–931, "Synthése De Dihalométhylcétones Par Action Des Carbénoïdes Sur Les Esters", Mar. 25, 1974.

Ping Chen, et al., Tetrahedron Letters, vol. 38, No. 18, pp. 3175–3178, "A Practical Method for the Preparation of α'–Chloroketones of N–Carbamate Protected–α–Aminoacids", 1997.

José Barluenga, et al., J. Chem. Soc., Chem. Commun., pp. 969–970, "The First Direct Preparation of Chiral Functionalised Ketones and Their Synthetic Uses", 1994.

Conrad J. Kowalski, et al., J. Org. Chem. vol. 50, No. 25, pp. 5140–5142, "Bromomethyl Ketones and Enolates: Alternative Products From Ester Homologation Reactions", 1985.

Jean Villieras et al. "Formation and reactivity of .alpha., alpha–dibromoalkyllithium reagents" Bull. Soc. Chim. Fr. 1975, vol. 7–8, Pt. 2, p. 1797–1802.

Cathy Bacquet et al. "Synthesis of dihalomethyl ketones by the action of carbenoids on esters", C.R. Acad. Sci. Sec. C, 1974, vol. 278, No. 13, p. 929–931.

* cited by examiner

Primary Examiner—Johann Richter
Assistant Examiner—Paul A. Zucker
(74) Attorney, Agent, or Firm—Oblon, Spivak, McClelland, Maier & Neustadt, P.C.

(57) ABSTRACT

A process for producing α-amino-dihalogenated methyl ketone derivatives by reacting an N-protected α-amino acid ester with a dihalomethyl lithium is provided. This process is suitable for the production on an industrial scale and by this process, α-amino-dihalogenated methyl ketone derivatives and β-amino-α-hydroxycarboxylic acid derivatives can be obtained efficiently and economically advantageously.

19 Claims, No Drawings

PROCESS FOR PRODUCING α-AMINOKETONE DERIVATIVES

This application is a Continuation International Application PCT/JP00/01498 filed on Mar. 13, 2000.

BACKGROUND OF THE INVENTION

The present invention relates to a process for producing α-amino-dihalogenated methyl ketone derivatives from N-protected α-amino acid esters.

The present invention also relates to a process for producing β-amino-α-hydroxycarboxylic acid derivatives from the α-amino-dihalogenated methyl ketone derivatives.

It was reported that α-amino-dihalogenated methyl ketone derivatives can be easily converted into β-amino-α-hydroxycarboxylic acid derivatives by hydrolysis in the presence of a base (see J.P. KO-KAI No. Hei 10-59909). β-Amino-α-hydroxycarboxylic acid derivatives obtained by this reaction are important compounds as intermediates for inhibitors of enzymes, such as HIV protease and renin or for some anticancer drugs (see, for example, Chem. Pharm. Bull. 1992, 40, 2251, J. Med. Chem. 1990, 33, 2707, Biochem. Pharmacol. 1983, 32, 1051, and Bull. Cancer 1993, 80, 326).

As for processes for producing α-amino-dihalogenated methyl ketone derivatives, it is described in an Example of J.P. KOKAI No. Hei 10-59909 that an N-carbamate-protected α-amino-dichloromethyl ketone derivative is produced by treating an α-amino-monochloromethyl ketone derivative, in which the amino group is protected with a carbamate-type protecting group, with sulfuryl chloride. However, this process is unsuitable for the production of a compound having a protecting group (such as t-butoxycarbonyl group) for an amino group, which is unstable against acids, because a strong acid is formed in the reaction system. In addition, the production of N-carbamate-protected α-amino-monochloromethyl ketone derivatives used as the starting material is not always easy.

DISCLOSURE OF THE INVENTION

The object of the present invention is to provide an economical, efficient process for producing α-amino-dihalogenated methyl ketone derivatives and β-amino-α-hydroxycarboxylic acid derivatives on an industrial scale.

After intensive investigations made for the purpose of solving the above-described problems, the inventors have found that α-amino-dihalogenated methyl ketones can be easily obtained by reacting an N-protected α-amino acid ester with a dihalomethyl lithium. The present invention has been completed on the basis of this finding.

Namely, the present invention provides a process for producing α-amino-dihalogenated methyl ketone derivatives of the following general formula (3):

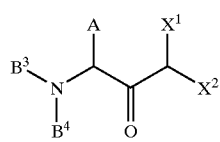

wherein $B^3$ and $B^4$ independently represent a hydrogen atom or a protecting group for an amino group, or $B^3$ and $B^4$ together form an imine-type protecting group; A represents a hydrogen atom, an unsubstituted or substituted alkyl group having 1 to 10 carbon atoms, aryl group having 6 to 15 carbon atoms or aralkyl group having 7 to 20 carbon atoms, or a group corresponding thereto which contains a hetero atom in the carbon skeleton; and $X^1$ and $X^2$ independently represent a chlorine atom or a bromine atom, which comprises the step of reacting an N-protected α-amino acid ester of following general formula (1):

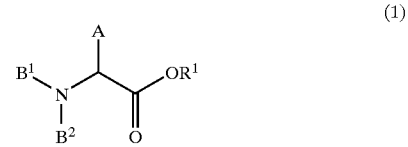

wherein $B^1$ and $B^2$ independently represent a hydrogen atom or a protecting group for an amino group, or $B^1$ and $B^2$ together form an imine-type protecting group (with the proviso that both $B^1$ and $B^2$ cannot be hydrogen atom at the same time), $R^1$ represents an unsubstituted or substituted lower alkyl group, aralkyl group or aryl group, and A is as defined above, with a dihalomethyl lithium of general formula (2)

wherein $X^1$ and $X^2$ are as defined above.

The present invention also provides a process for producing β-amino-α-hydroxycarboxylic acid derivatives of general formula (4):

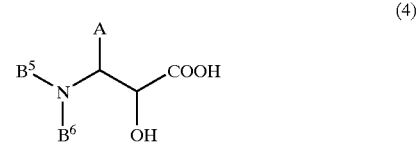

wherein $B^5$ and $B^6$ independently represent a hydrogen atom or a protecting group for an amino group, or $B^5$ and $B^6$ together form an imine-type protecting group, and A represents hydrogen atom, an unsubstituted or substituted alkyl group having 1 to 10 carbon atoms, aryl group having 6 to 15 carbon atoms or aralkyl group having 7 to 20 carbon atoms, or a group corresponding thereto which contains a hetero atom in the carbon skeleton, which comprises the steps of hydrolyzing an α-amino-dihalogenated methyl ketone derivative in the presence of a base and protecting or not protecting the amino group.

BEST MODE FOR CARRYING OUT THE INVENTION

In the formulae in the present invention, $B^1$ and $B^2$ independently represent a hydrogen atom or a protecting group for an amino group, or $B^1$ and $B^2$ together form an imine-type protecting group. However, both $B^1$ and $B^2$ cannot be hydrogen atom at the same time.

The protecting group for amino group is not particularly limited. For example, protecting groups described in Protecting Groups in Organic Chemistry, $2^{nd}$ Edition (John Wiley & Sons, Inc. 1991) are usable. The protecting groups are, for example, carbamate-type protecting groups such as a methoxycarbonyl group, a ethoxycarbonyl group, a t-butoxycarbonyl group, a benzyloxycarbonyl group, and a fluorenylmethoxycarbonyl group; acyl-type protecting groups such as an acetyl group and a benzoyl group; sulfonyl-type protecting groups, such as a methanesulfonyl group, a benzenesulfonyl group, and a p-toluenesulfonyl group; alkyl-type protecting groups, such as a benzyl group and a p-methoxybenzyl group; dialkyl-type protecting groups, such as, a dibenzyl group; silyl-type protecting groups, such as, a trimethylsilyl group; and imine-type protecting groups, such as, a diphenylmethylene group, a phenylmethylene group, and a p-methoxyphenylmethylene group. Among them, carbamate-type protecting groups are preferred because they can be easily removed.

When $B^1$ and $B^2$ together form an imine-type protecting group, N-protected α-amino acid esters of general formula (1) can be represented by following general formula (6):

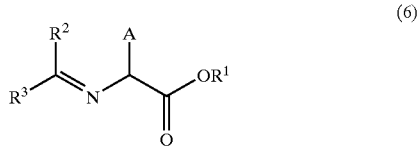

(6)

wherein $R^2$ and $R^3$ independently represent an unsubstituted or substituted aryl group or lower alkyl group or hydrogen atom, or $R^2$ and $R^3$ may be bonded together directly or via a suitable group to form a ring structure.

Examples of the ring structures include the following structures (16) and (17):

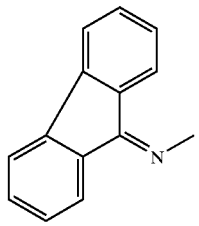

(16)

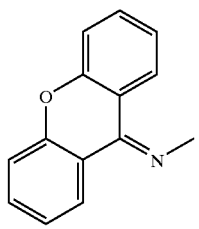

(17)

[Formulae (16) and (17) include both protecting group formed by $R^2$ and $R^3$ and the imine structure].

Preferably $R^2$ and $R^3$ each represent an unsubstituted or substituted aryl group or one of them represents an unsubstituted or substituted aryl group and the other represents a hydrogen atom.

The unsubstituted or substituted lower alkyl group, aralkyl group or aryl group represented by $R^1$ in the formula in the present invention include unsubstituted or substituted, linear or branched, saturated alkyl groups having 1 to 8 carbon atoms, unsubstituted or substituted aralkyl groups having 7 to 15 carbon atoms, and unsubstituted or substituted aryl groups having 6 to 14 carbon atoms. $R^1$ is preferably an unsubstituted or substituted lower alkyl group, or aralkyl group. $R^1$ is particularly preferably a linear or branched, saturated alkyl group having 1 to 3 carbon atoms, i.e. methyl group, ethyl group, propyl group, isopropyl group or unsubstituted or substituted benzyl group. When the benzyl group is substituted, the substituent is an alkoxyl group (preferably having 1 to 7 carbon atoms), nitro group, an alkyl group (preferably having 1 to 6 carbon atoms), a halogen atom or the like.

A in the formulae in the present invention represents a hydrogen atom, an unsubstituted or substituted alkyl group having 1 to 10 carbon atoms, aryl group having 6 to 15 carbon atoms or aralkyl group having 7 to 20 carbon atoms, or a corresponding group which further contains a hetero atom in the carbon skeleton. When those groups have a substituent, the substituent is an alkoxyl group (preferably having 1 to 7 carbon atoms), a nitro group, an alkyl group (preferably having 1 to 6 carbon atoms), a halogen atom or the like.

Such a group can be introduced into the compound from, e.g., an amino acid. For example, when A is hydrogen atom, it can be introduced by using glycine as the starting material. In the same way, a methyl group can be introduced by using alanine; an isopropyl group can be introduced by using valine; a 2-methylpropyl group can be introduced by using leucine; a 1-methylpropyl group can be introduced by using isoleucine; a benzyl group can be introduced by using phenylalanine; and a methylthioethyl group can be introduced by using methionine.

A may be a group introduced by using an amino acid in which a functional group in a side chain thereof is protected, such as S-t-butylcysteine, S-tritylcysteine, S-(p-methylbenzyl)cysteine, S-(p-methoxybenzyl)cysteine, O-t-butylserine, O-benzylserine, O-t-butylthreonine, O-benzylthreonine, O-t-butyltyrosine or O-benzyltyrosine, as the starting material.

A is not limited to a group introduced from a starting material derived from a natural amino acid, but it may a group introduced from a starting material derived from a synthetic amino acid (such as a cyclohexylmethyl group, a phenyl group, or a phenylthiomethyl group).

Preferably A represents an unsubstituted or substituted alkyl group having 1 to 10 carbon atoms, aryl group having 6 to 15 carbon atoms or aralkyl group having 7 to 20 carbon atoms, or a group corresponding thereto which contains a hetero atom in the carbon skeleton.

In the formulae in the present invention, $X^1$ and $X^2$ independently represent a chlorine atom or a bromine atom. It is preferred that both $X^1$ and $X^2$ represent chlorine atom or bromine atom. It is particularly preferred that both $X^1$ and $X^2$ represent chlorine atom.

In the formula in the present invention, $B^3$ and $B^4$ independently represent hydrogen atom or a protecting group for amino group, or $B^3$ and $B^4$ together form an imine-type protecting group. The protecting groups for amino group are as described above. The imine-type protecting groups are also as described above.

In the formula in the present invention, $B^5$ and $B^6$ independently represent a hydrogen atom or a protecting group for an amino group, or $B^5$ and $B^6$ together form an imine-type protecting group. The protecting groups for amino group are as described above. The imine-type protecting groups are also as described above.

N- protected α-amino acid esters of general formula (1) used as the starting material in the present invention can be produced from α-amino acid esters and salts thereof or α-amino acids by a known process.

N-carbamate-protected α-amino acid esters particularly preferably used as the starting compounds in the present invention can be easily synthesized from α-amino acid esters and salts thereof by an ordinary technique of synthesizing peptides.

When N-protected α-amino acid esters of general formula (1) are in a form protected with an imine-type protecting group as shown in above general formula (6), they can be easily produced from an α-amino acid ester of general formula (7) or a salt thereof and an imine compound of general formula (8) or an aldehyde or ketone compound of general formula (9) by a known method (see, for example, A. Dondoni et al., Synthesis 1993, 1162 and M. J. O'Donnel et al., J. Org. Chem. 1982, 47, 2663) according to the following scheme:

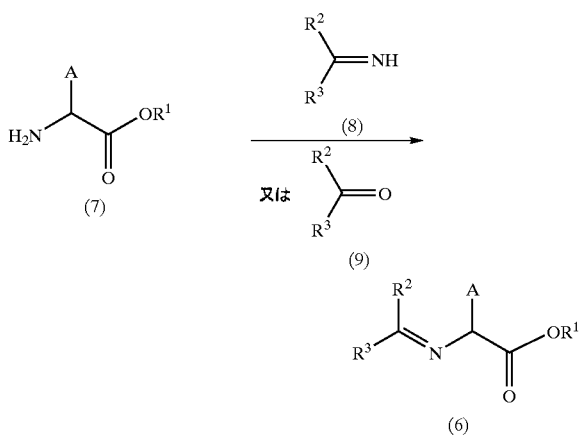

wherein $R^1$, $R^2$, $R^3$ and A are as defined above.

The production process of the present invention can be employed for synthesizing optically active compounds by using an optically active α-amino acid ester obtained by esterifying an optically active amino acid. Optically active amino acids are important in the field of medicines. Namely, optically active compounds (L- and D-compounds) are preferably used as the α-amino acid esters. In particular, optically active phenylalanine esters are important starting materials of HIV protease inhibitors.

Now, the description will be made on the process for producing α-amino-dihalogenated methyl ketones of general formula (3) by reacting an N-protected α-amino acid ester of general formula (1) with a dihalomethyl lithium of general formula (2).

A dihalomethyl lithium of general formula (2) can be produced from a dihalomethane of general formula (10) and a lithium amide of general formula (11) according to the following scheme:

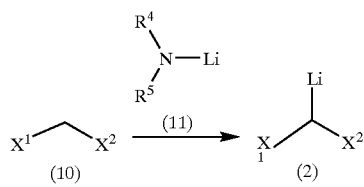

wherein $X^1$ and $X^2$ are as defined above, $R^4$ and $R^5$ independently represent an alkyl group or a trialkylsilyl group and $R^4$ and $R^5$ may be bonded together directly or via a suitable group to form a ring structure.

Examples of the alkyl groups include a methyl group, an ethyl group, an isopropyl group, and a cyclohexyl group. The trialkylsilyl groups include, for example, a trimethylsilyl group. An example of the ring structures is shown by the following formula (12):

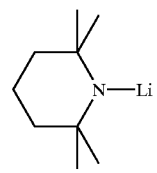

The dihalomethane of general formula (10) is any of dichloromethane, dibromomethane and bromochloromethane. Preferred examples of the lithium amides of general formula (11) include lithium dimethylamide, lithium diethylamide, lithium diisopropylamide, lithium dicyclohexylamide, lithium 2,2,6,6-tetramethyl piperidide and lithium bis(trimethylsilyl)amide. Lithium diisopropylamide is particularly preferred.

It is known from U.S. Pat. No. 5,481,011 and Tetrahedron Letters, 38, 3175–3178, 1997 that an N-protected α-amino acid ester is reacted with chloroiodomethane and lithium diisopropylamide to form N-protected α-amino-monochloromethyl ketone. In this reaction, an exchange reaction of an iodine atom with lithium must be carried out in the obtained intermediate in order to obtain monochloromethyl ketone (see the reaction scheme on page 3175 of the above-described Tetrahedron Letters).

According to the Tetrahedron Letters publication (38, 3175–3178, 1997), at least 4 equivalents of chloroiodomethane and also at least 4 equivalents of lithium diisopropylamide are [necessitated] necessary. It is described therein that for attaining the optimum conditions, 4 equivalents of chloroiodomethane and 5 equivalents of lithium diisopropylamide are to be used.

In the present invention, such an exchange reaction must be prevented for synthesizing N-protected α-amino-dihalomethyl ketones. Namely, in the present invention, the amount of a dihalomethyl lithium (particularly dibromomethyl lithium or bromochloromethyl lithium) to be reacted with an N-protected α-amino acid ester is preferably 2 equivalents to less than 3 equivalents, more preferably 2.2 equivalents to 2.8 equivalents, particularly 2.4 equivalents to 2.6 equivalents.

Therefore, in the production of a dihalomethyl lithium from a dihalomethane and a lithium amide, the amount of each of dihalomethane and lithium amide is preferably 2 equivalents to less than 3 equivalents, more preferably 2.2 equivalents to 2.8 equivalents, particularly 2.4 equivalents to 2.6 equivalents.

In the production of an N-protected α-amino-dihalomethyl ketone from an N-protected α-amino acid ester and dichloromethyllithium, the above-described exchange reaction does not occur.

In the dihalomethyl lithiums, dichloromethyl lithium can be produced from dichloromethane and an organic lithium of general formula (13) according to the following scheme:

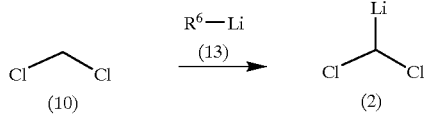

wherein $R^6$ represents a lower alkyl group or an aryl group.

The lower alkyl groups include a linear or branched, saturated alkyl groups having 1 to 8 carbon atoms. Linear, saturated alkyl groups having 1 to 6 carbon atoms, i.e. a methyl group, an ethyl group, an n-butyl group, a sec-butyl group, and a n-hexyl group, are particularly preferred.

The aryl groups are, for example, a phenyl group and a naphthyl group.

Lower alkyllithiums of the above formula wherein $R^6$ represents a lower alkyl group are preferred. Those where $R^6$ represents a linear, saturated alkyl group having 1 to 6 carbon atoms, i.e. a methyl group, an ethyl group, an n-butyl group, a sec-butyl group, and a n-hexyl group, are particularly preferred.

The N-protected α-amino acid ester is reacted with the dihalomethyl lithium.

The following two reaction procedures are possible:

(1) A dihalomethyl lithium is previously produced by reacting a lithium amide or an organic lithium compound with a dihalomethane. Then, an N-protected α-amino acid ester is added thereto. When both $B^1$ and $B^2$, which are protecting groups for amino group, are not hydrogen [atom] atoms, this reaction procedure is preferred. The reaction temperature is preferably about −120° C. to −50° C.

(2) A dihalomethane is reacted with a lithium amide or an organic lithium compound in the presence of an N-protected α-amino acid ester to form a dihalomethyl-lithium in the reaction system. The reaction temperature is preferably about −120° C. to +10° C. The reaction can be carried out at a relatively high temperature such as −20° C.

When this reaction procedure is employed, a carbamate-type protecting group is preferred.

The reaction solvent is preferably an ether solvent such as tetrahydrofuran, diethyl ether, or t-butyl methyl ether. If necessary, the solvent can be used in the form of a mixture thereof with a non-polar solvent, such as toluene or hexane. The reaction rapidly proceeds at a temperature of about −120° C. to +10° C. Usually, the reaction is completed at −80° C. to −20° C. in 5 to 60 minutes. After the completion of the reaction, the reaction mixture is treated with an aqueous ammonium chloride solution, a phosphate buffer, a dilute hydrochloric acid solution, a dilute sulfuric acid solution, or the like.

The protecting group for the amino group is either removed or not removed depending on the combination of the reaction conditions with the protecting group. The amino group may be kept as it is without the protecting group or another protecting group may be introduced by a well-known method. The carbamate-type protecting group preferably used in the present invention can be usually kept as it is when the compound is reacted as will be described in the Examples given below.

Then, the reaction product is extracted from the reaction solution with a solvent such as ethyl acetate, diethyl ether, toluene, isopropyl acetate, tert-butyl methyl ether, dichloromethane, or chloroform. Then, if necessary, the obtained solution is concentrated (or evaporated). If necessary, a solvent such as methanol, ethanol, 2-propanol, acetonitrile, tetrahydrofuran, hexane, heptane or acetone is added to the product. The obtained solution is heated to about 40 to 80° C. The α-amino-dihalogenated methyl ketone derivative can be obtained in solid form by the crystallization by cooling to a temperature of −20° C. to room temperature or by a chromatography. The product may be used for the subsequent reaction without being separated or purified.

α-Amino-dihalogenated methyl ketone derivatives of general formula (3) can be easily converted into, β-amino-α-hydroxycarboxylic acid derivatives by hydrolysis in the presence of a base, as described in J. P. KOKAI No. Hei 10-59909. In this case, the protecting group for the amino group is either removed or kept depending on the combination of the reaction conditions with the protecting group. The compound thus obtained may be isolated as it is without the protecting group or another protecting group may be introduced. When another protecting group is introduced, the introduction can be conducted by, for example, a process described in J. P. KOKAI No. Hei 10-59909. β-amino-α-hydroxycarboxylic acid derivatives are important compounds as intermediates for enzyme inhibitors, such as HIV protease and rennin, or some anticancer drugs.

The compounds in the present invention also include racemic compounds and both optically active compounds. When an optically active N-protected α-amino acid ester is used as the N-protected α-amino acid ester of general formula (1), a compound of general formula (3) obtained by the process of the present invention maintains its optical activity. Further, compounds of general formula (4) produced from the above-described compounds of general formula (3) also maintain their optical activity. Therefore, the process of the present invention is very useful for the synthesis of intermediate compounds for medicines.

The following Examples will further illustrate the present invention, which by no means limit the invention.

EXAMPLES

Reference Example 1

A Process for Producing Methyl Ester of N-tert-butoxycarbonyl-L-phenylalanine

L-Phenylalanine methyl ester hydrochloride (21.6 g) was added to a mixed solution of methanol (50 ml) and water (100 ml). Sodium carbonate (11.64 g) and then a solution of di-tert-butoxy dicarbonate (21.8 g) in methanol (100 ml) were added to the obtained mixture. They were heated to 40° C. and stirred for 6 hours. The reaction mixture was concentrated and the methanol was evaporated. The ethyl [Ethyl] acetate and water were added to the obtained concentrate to conduct the extraction. Ethyl acetate layer thus obtained was washed with 0.1 N hydrochloric acid, water, an aqueous sodium hydrogencarbonate solution and a saturated aqueous sodium chloride solution. The obtained ethyl acetate layer was dried over anhydrous magnesium sulfate. Magnesium sulfate was filtered out. The solvent was evaporated under reduced pressure to obtain the intended methyl ester of N-tert-butoxycarbonyl-L-phenylalanine (26.4 g) in a yield of 95%.

$^1$H-NMR(CDCl$_3$, 300 MHz) δ ppm: 1.39 (s, 9H), 2.98–3.16 (m, 2H), 3.69 (s, 3H), 4.54–4.65 (m, 1H), 4.93–5.03 (bd, 1H), 7.08–7.32 (m, 5H)

Example 1

A Process for Producing (3S)-3-tert-butoxycarbonylamino-1,1-dichloro-4-phenyl-2-butanone Dehydrated tetrahydrofuran (15 ml) was cooled to −78° C. 2M solution (5.75 ml) of lithium diisopropylamide in heptane, tetrahydrofuran and ethylbenzene was added thereto. A solution of methylene chloride (0.74 ml) in dehydrated tetrahydrofuran (5 ml) was added to the obtained mixture. They were stirred for 10 minutes. Then a solution of N-tert-butoxycarbonyl-L-phenylalanine methyl ester (1.4 g) in dehydrated tetrahydrofuran (7 ml) was added to the mixture, and they were stirred for 1 hour. 1 N hydrochloric acid (25 ml) was added to the reaction mixture to terminate the reaction. The temperature was elevated to room temperature. After the extraction with ethyl acetate and water, the obtained solution in ethyl acetate was analyzed by HPLC to find that the intended (3S)-3-tert-butoxycarbonylamino-1,1-dichloro-4-phenyl-2-butanone (1.31 g) was obtained in a yield of 79%. After HPLC with an optically active column, the optical purity of (3S)-3-tert-butoxycarbonylamino-1,1-dichloro-4-phenyl-2-butanone in the ethyl acetate solvent was found to be >99.5% e.e. The obtained solution in ethyl acetate was dried over anhydrous magnesium sulfate. Magnesium sulfate was filtered off. The solvent was evaporated under reduced pressure. Ethyl acetate was added to the residue to form a slurry. The crystals thus formed were separated from the slurry and dried to obtain the intended (3S)-3-tert-butoxycarbonylamino-1,1-dichloro-4-phenyl-2-butanone (1.12 g) in a yield of 67%.

The obtained (3S)-3-tert-butoxycarbonylamino-1,1-dichloro-4-phenyl-2-butanone was analyzed by HPLC with an optically active column to find that the optical purity thereof was >99.5% e.e.

$^1$H-NMR(CDCl$_3$, 300 MHz) δ ppm: 1.40(s,9H), 3.01 (dd,J=7.9, 13.8 Hz, 1H), 3.22 (dd,J=5.7, 13.8 Hz, 1H), 4.62–5.00 (m, 2H), 6.08(s, 1H), 7.17–7.22(m, 2H), 7.22–7.36(m, 3H) $[\alpha]_D^{20}$=−52.7° (c=2.25, CH$_2$Cl$_2$)

Example 2

A Process for producing (3S)-tert-butoxycarbonylamino-1,1-dichloro-4-phenyl-2-butanone Methyl ester (1.4 g) of N-tert-butoxycarbonyl-L-phenylalanine (1.4 g) was dissolved in dehydrated tetrahydrofuran (20 ml), and the obtained solution was cooled to −78° C. Methylene chloride (0.64 ml) and then 2 M solution (7.5 ml) of lithium diisopropylamide in heptane, tetrahydrofuran and ethylbenzene were added thereto, and they were stirred for 1 hour. A saturated aqueous ammonium chloride solution (20 ml) was added to the reaction mixture to terminate the reaction. The temperature was elevated to room temperature. After the extraction with ethyl acetate and water, the obtained solution in ethyl acetate was analyzed by HPLC to find that the intended (3S)-3-tert-butoxycarbonylamino-1,1-dichloro-4-phenyl-2-butanone (0.86 g) was obtained in a yield of 52%. The obtained solution in ethyl acetate was dried over anhydrous magnesium sulfate. Magnesium sulfate was filtered off. The solvent was evaporated under reduced pressure. Ethyl acetate was added to the residue to form a slurry. The crystals thus formed were separated from the slurry and dried to obtain the intended (3S)-3-tert-butoxycarbonylamino-1,1-dichloro-4-phenyl-2-butanone (0.65 g) in a yield of 36%.

The obtained (3S)-3-tert-butoxycarbonylamino-1,1-dichloro-4-phenyl-2-butanone was analyzed by HPLC with an optically active column to find that the optical purity thereof was >99.5% e.e.

Example 3

A Process for Producing (3S)-3-tert-butoxycarbonylamino-1,1-dichloro-4-phenyl-2-butanone Methyl ester (1.40 g) of N-tert-butoxycarbonyl-L-phenylalanine was dissolved in dehydrated tetrahydrofuran (27 ml) and methylene chloride (0.80 ml), and the obtained solution was cooled to −20° C. 2M solution (6.25 ml) of lithium diisopropylamide in heptane, tetrahydrofuran and ethylbenzene were added thereto, and they were stirred for 1 hour. 2 N Hydrochloric acid (12.5 ml) and water (12.5 ml) were added to the reaction mixture to terminate the reaction. The temperature was elevated to room temperature. After the extraction with ethyl acetate and water, the obtained solution in ethyl acetate was analyzed by HPLC to find that the intended (3S)-3-tert-butoxycarbonylamino-1,1-dichloro-4-phenyl-2-butanone (0.94 g) was obtained in a yield of 57%. The obtained solution in ethyl acetate was dried over anhydrous magnesium sulfate. Magnesium sulfate was filtered off. The solvent was evaporated under reduced pressure. Ethyl acetate was added to the residue to form a slurry. The crystals thus formed were separated from the slurry and dried to obtain the intended (3S)-3-tert-butoxycarbonylamino-1,1-dichloro-4-phenyl-2-butanone (0.77 g) in a yield of 46%.

The obtained (3S)-3-tert-butoxycarbonylamino-1,1-dichloro-4-phenyl-2-butanone was analyzed by HPLC with an optically active column to find that the optical purity thereof was >99.5% e.e.

Example 4

A Process for Producing (3S)-3-tert-butoxycarbonylamino-1,1-dichloro-4-phenyl-2-butanone Dehydrated tetrahydrofuran (19.5 ml) was cooled to −78° C. 1.53 M solution (13.1 ml) of n-butyllithium in hexane was added thereto. A solution of methylene chloride (1.28 ml) in dehydrated tetrahydrofuran (6.9 ml) was added to the obtained mixture and they were stirred for 10 minutes. A solution of methyl ester (1.40 g) of N-tert-butoxycarbonyl-L-phenylalanine in dehydrated tetrahydrofuran (6.9 ml) was added thereto and they were stirred for 1 hour. 10% aqueous sulfuric acid solution (10.7 ml) was added to the reaction mixture to terminate the reaction. The temperature was elevated to room temperature. After the extraction with ethyl acetate, the obtained solution in ethyl acetate was analyzed by HPLC to find that the intended (3S)-3-tert-butoxycarbonylamino-1,1-dichloro-4-phenyl-2-butanone (1.00 g) was obtained in a yield of 60%. The obtained (3S)-3-tert-butoxycarbonylamino-1,1-dichloro-4-phenyl-2-butanone in ethyl acetate solvent was analyzed by HPLC with an optically active column to find that the optical purity thereof was >99.5% e.e. The obtained solution in ethyl acetate was dried over anhydrous magnesium sulfate. Magnesium sulfate was filtered off. The solvent was evaporated under reduced pressure. Ethyl acetate was added to the residue to form a slurry. The crystals thus formed were separated from the slurry and dried to obtain the intended (3S)-3-tert-butoxycarbonylamino-1,1 dichloro-4-phenyl-2-butanone (0.90 g) in a yield of 54%.

Example 5

A Process for Producing (3S)-3-tert-butoxycarbonylamino-1,1-dichloro-4-phenyl-2-butanone Methyl ester (1.40 g) of N-tert-butoxycarbonyl-L-phenylalanine was dissolved in dehydrated tetrahydrofuran (33.3 ml). Methylene chloride (1.28 ml) was added to the obtained solution and they were cooled to −78° C. 1.53 M solution (13.1 ml) of n-butyllithium in hexane was added thereto and they were stirred for 1 hour. 10% aqueous sulfuric acid solution (10.7 ml) was added to the reaction mixture to terminate the reaction. The temperature was elevated to room temperature. After the extraction with ethyl acetate, the obtained solution in ethyl acetate was analyzed by HPLC to find that intended (3S)-3-tert-butoxycarbonylamino-1,1-dichloro-4-phenyl-2-butanone (1.03 g) was obtained in a yield of 62%. The obtained (3S)-3-tert-butoxycarbonylamino-1,1-dichloro-4-phenyl-2-butanone in ethyl acetate solvent was analyzed by HPLC with an optically active column to find that the optical purity thereof was >99.5% e.e. The obtained solution in ethyl acetate was dried over anhydrous magnesium sulfate. Magnesium sulfate was filtered off. The solvent was evaporated under reduced pressure. Ethyl acetate was added to the residue to form a slurry. The crystals were separated from the slurry and dried to obtain the intended (3S)-3-tert-butoxycarbonylamino-1,1-dichloro-4-phenyl-2-butanone (0.87 g) in a yield of 52%.

Example 6

A Process for Producing (3S)-3-tert-butoxycarbonylamino-1,1-dichloro-4-phenyl-2-butanone A mixed solution of dehydrated tetrahydrofuran (6.4 ml) and diethyl ether (7 ml) was cooled to −78° C. 1.53 M solution (6.5 ml) of n-butyllithium in hexane was added to the mixed solution and they were stirred for 10 minutes (reaction solution A).

Methyl ester (1.40 g) of N-tert-butoxycarbonyl-L-phenylalanine was dissolved in a mixture of dehydrated tetrahydrofuran (6.4 ml) and diethyl ether (7 ml), and the obtained mixture was cooled to −78° C. 1.53 M solution (3.3 ml) of n-butyllithium in hexane was added to the mixture. Trimethylsilane (0.72 ml) was added to the obtained mixture and the temperature was elevated to room temperature (reaction solution B).

Reaction solution B was added to reaction solution A, and they were stirred at −78° C. for 1.5 hours (reaction solution C). Saturated aqueous ammonium chloride solution (20 ml) was added to reaction solution C to terminate the reaction. The temperature was elevated to room temperature. After the extraction with ethyl acetate and water, the obtained solution in ethyl acetate was analyzed by HPLC to find that the intended (3S)-3-tert-butoxycarbonylamino-1,1-dichloro-4-phenyl-2-butanone (0.88 g) was obtained in a yield of 53%. The obtained solution in ethyl acetate solvent was dried over anhydrous magnesium sulfate. Magnesium sulfate was filtered out. The solvent was evaporated under reduced pressure. A mixed solvent of ethyl acetate and n-hexane was added to the residue to obtain a slurry. Crystals thus obtained were separated and dried to obtain the intended (3S)-3-tert-butoxycarbonylamino-1,1-dichloro-4-phenyl-2-butanone (0.65 g) in a yield of 39%. This compound was analyzed by HPLC with an optically active column to find that the optical purity thereof was >99.5% e.e.

Example 7

A Process for Producing (2S,3S)-3-tert-butoxycarbonylamino-2-hydroxy-4-phenylbutanoic acid (3S)-3-Tert-butoxycarbonylamino-1,1-dichloro-4-phenyl-2-butan one (1.71 g) was added to toluene (13 ml), and they were stirred at room temperature. 2 N Aqueous sodium hydroxide solution (12.9 ml) was added to the obtained mixture, and they were stirred at 50° C. for 1 hour. After cooling to room temperature, the aqueous layer was separated. The toluene layer was washed with water (5 ml), and the obtained aqueous layers were combined together and then analyzed by HPLC to find that the 3-tert-butoxycarbonylamino-2-hydroxy-4-phenylbutanoic acid (1.20 g) was obtained in a yield of 79%. According to the HPLC analysis, the ratio of intended (2S,3S)-3-tert-butoxycarbonylamino-2-hydroxy-4-phenylbutanoic acid to its isomer (2R,3S) was as follows: (2S,3S):(2R,3S)= 76.6:23.4.6 N Hydrochloric acid was added to the aqueous layer to control pH at 2.4. After the extraction with ethyl acetate twice, the obtained ethyl acetate layers were combined together and washed with saturated aqueous sodium chloride solution. The obtained solution in ethyl acetate was dried over anhydrous magnesium sulfate. Magnesium sulfate was filtered out. The solvent was evaporated under reduced pressure. Ethyl acetate (13 ml) was added to the residue and they were heated to 65° C. to obtain a solution. n-Hexane (8 ml) was added to the obtained solution, and they were slowly cooled to 5° C. to form crystals. The crystals thus obtained were separated and washed with a mixed solution of ethyl acetate and hexane. After drying, the intended (2S,3S)-3-tert-butoxycarbonylamino-2-hydroxy-4-phenyl-2-butanoic acid (0.75 g) was obtained in a yield of 50%. According to HPLC analysis, the ratio of (2S,3S)-3-tert-butoxycarbonylamino-2-hydroxy-4-phenylbutanoic acid to its isomer.(2R,3S) in the obtained crystals was as follows: (2S,3S):(2R,3S)=99.6:0.4. (2S,3S)-3-Tert-butoxycarbonylamino-2-hydroxy-4-phenylbutanoic acid thus obtained was analyzed by HPLC with an optically active column to find that the optical purity thereof was >99.5% e.e.

$^1$H-NMR(CDCl$_3$, 300 MHz) δ ppm: 1.40(s,9H), 2.93–3.04(m,2H), 4.15(ddd,J=2.2, 7.7, 10.2 Hz, 1H), 4.35 (d, J=2.2 Hz, 1H), 4.90 (bs, 1H), 7.20–7.35 (m, 5H) [α]$_D^{20}$=−17.3° (c=1.0, MeOH)

Example 8

A Process for Producing (3S)-1,1-dibromo-3-tert-butoxycarbonylamino-4-phenyl-2-butanone Dehydrated tetrahydrofuran (15 ml) was cooled to 78° C. 2M solution (6.25 ml) of lithium diisopropylamide in heptane, tetrahydrofuran and ethylbenzene was added thereto. Then a solution of dibromomethane (0.88 ml) in dehydrated tetrahydrofuran (5 ml) was added to the obtained mixture, and they were stirred for 10 minutes.

A solution of methyl ester (1.4 g) of N-tert-butoxycarbonyl-L-phenylalanine in dehydrated tetrahydrofuran (7 ml) was added to the obtained mixture, and they were stirred for 1 hour. 1 N hydrochloric acid (25 ml) was added to the reaction mixture to terminate the reaction. The temperature was elevated to room temperature. After the extraction with ethyl acetate, the obtained solution in ethyl acetate was analyzed by HPLC to find that the intended (3S)-1,3-dibromo-3-tert-butoxycarbonylamino-4-phenyl-2-butanone (1.14 g) was obtained in a yield of 53% The obtained solution in ethyl acetate solvent was dried over anhydrous magnesium sulfate. Magnesium sulfate was filtered out. The solvent was evaporated under reduced pressure. Ethyl acetate was added to the residue to obtain a slurry. Crystals thus obtained were separated and dried to obtain the intended (3S)-1,1-dibromo-3-tert-butoxycarbonylamino-4-phenyl-2-butanone (1.04 g) in a yield of 46%.

$^1$H-NMR(CDCl$_3$, 300 MHz) δ ppm: 1.41 (s, 9H), 3.04 (dd, J=7.3, 13.8 Hz, 1H), 3.20 (dd, J=6.2, 13.8 Hz, 1H), 4.64–5.05 (m, 2H), 6.00 (s, 1H), 7.17–7.37 (m, 5H) [α]$_D^{20}$=–40.6° (c=2.0, CH$_2$Cl$_2$)

Example 9

A Process for Producing (2S,3S)-3-tert-butoxycarbonylamino-2-hydroxy-4-phenylbutanoic acid (3S)-1,1-Dibromo-3-tert-butoxycarbonylamino-4-phenyl-2-butan one (0.20 g) was added to toluene (1.2 ml), and they were stirred at room temperature. 2 N Aqueous sodium hydroxide solution (1.2 ml) was added to the obtained mixture, and they were stirred for additional 3 hours. Then toluene and water were added to the reaction mixture. The aqueous layer was separated and analyzed by HPLC to find that 3-tert-butoxycarbonylamino-2-hydroxy-4-phenylbutanoic acid (0.12 g) was obtained in a yield of 85%. According to the HPLC analysis, the ratio of intended (2S,3S)-3-tert-butoxycarbonylamino-2-hydroxy-4-phenyl-butanoic acid to its isomer (2R,3S) was as follows: (2S,3S): (2R,3S)=81.5:18.5.

Example 10

A Process for Producing (2S,3S)-3-tert-butoxycarbonylamino-2-hydroxy-4-phenylbutanoic acid (3S)-1,1-Dibromo-3-tert-butoxycarbonylamino-4-phenyl-2-butanone (100 mg) was added to toluene (0.595 ml), and they were stirred at room temperature. 2 N Aqueous sodium hydroxide solution (0.595 ml) was added to the obtained mixture, and they were stirred at 50° C. for additional 50 minutes. After cooling to room temperature, toluene and water were added to the reaction mixture. The aqueous layer was separated and analyzed by HPLC to find that 3-tert-butoxycarbonylamino-2-hydroxy-4-phenylbutanoic acid (56 mg) was obtained in a yield of 80%. According to the HPLC analysis, the ratio of the intended (2S,3S)-3-tert-butoxycarbonylamino-2-hydroxy-4-phenyl-butanoic acid to its isomer (2R,3S) was as follows: (2S,3S): (2R,3S)=80.3:19.7.

Referential Example 2

A Process for Producing Methyl Ester of N-(diphenylmethylene)-L-phenylalanine

Hydrochloride of methyl ester of L-phenylalanine (5.95 g) and benzophenoneimine (5.00 g) were added to methylene chloride (100 ml), and they were stirred at room temperature overnight. A solid thus formed was filtered out of the reaction mixture. The filtrate was concentrated under reduced pressure. Diethyl ether (100 ml) was added to the residue. A solid thus formed was again filtered out of the reaction mixture. The ether layer was washed with water (100 ml) and then dried over anhydrous magnesium sulfate. Magnesium sulfate was removed, and the solution in ether was concentrated to obtain the intended methyl ester of N-(diphenylmethylene)-L-phenylalanine (9.44 g) in a yield of 99.6%.

1H-NMR(CDCl$_3$, 300 MHz) δ ppm: 3.17 (dd, J=9.0, 13.5 Hz, 1H), 3.27 (dd, J=3.9, 13.5 Hz, 1H), 3.70 (s, 3H), 4.27 (dd, J=3.9, 9.0 Hz, 1H), 6.58 (d, J=9.0 Hz, 2H), 7.01–7.04 (m, 2H), 7.16–7.19 (m, 3H), 7.25–7.41 (m, 6H), 7.58 (d, J=6.0 Hz, 2H)

Example 11

A Process for Producing (3S)-1,1-dichloro-3-(diphenylmethylene)amino-4-phenyl-2-butanone A mixed solution of dehydrated tetrahydrofuran (6.2 ml) and diethyl ether (3.1 ml) was cooled to −78° C. 1.53 M solution (3.3 ml) of n-butyllithium in hexane and then a solution of methylene chloride (0.40 ml) in dehydrated tetrahydrofuran (3.3 ml) were added to the mixed solution and they were stirred for 10 minutes. Then a solution of methyl ester of N-(diphenylmethylene)-L-phenylalanine (0.86 g) in diethyl ether (3.3 ml) was added to the obtained solution. They were stirred for 2 hours. Saturated aqueous ammonium chloride solution was added to the reaction solution to terminate the reaction. The temperature was elevated to room temperature. After the addition of water followed by the extraction with ethyl acetate twice, the obtained solutions in ethyl acetate were combined together and washed with saturated aqueous sodium chloride6solution. The obtained solution in ethyl acetate solvent was dried over anhydrous magnesium sulfate. Magnesium sulfate was filtered out. The solvent was evaporated under reduced pressure to obtain the intended (3S)-1,1-dichloro-3-(diphenylmethylene) amino-4-phenyl-2-butanone (0.95 g) in a yield of 96%.

1H-NMR(CDCl$_3$, 300 MHz) δ ppm: 3.12 (dd, J=4.6, 13.2 Hz, 1H), 3.20 (dd, J=8.4, 13.2 Hz, 1H), 4.56 (dd, J=4.6, 8.4 Hz, 1H), 6.52 (d, J=9.9 Hz, 2H), 6.53 (s, 1H), 6.96–7.05 (m, 2H), 7.15–7.47 (m, 9H), 7.61 d, J=9.1 Hz, 2H)

Referential Example 3

A Process for Producing Benzyl Ester of N,N-dibenzyl-L-phenylalanine

L-Phenylalanine (16.5 g) and potassium carbonate (27.6 g) were added to a mixed solvent of methanol (100 ml) and water (100 ml). Then, benzyl bromide (68.4 g) was added to the obtained mixture, and they were stirred under heating and reflux for 3 hours. The reaction mixture was cooled to room temperature, and poured on ice/water. After the extraction with diethyl ether (300 ml), the obtained solution in diethyl ether was dried over anhydrous sodium sulfate. Sodium sulfate was filtered out. 4 N solution (25 ml) of dioxane in hydrochloric acid was added to the obtained solution in diethyl ether. After stirring under cooling on ice followed by the crystallization, the crystals were separated and washed with diethyl ether. The obtained crystals were added to a mixture of water (100 ml) and toluene (100 ml) to obtain a slurry. After the neutralization with a saturated aqueous sodium hydrogencarbonate solution followed by the division into layers, the product was extracted again with toluene. The obtained toluene layers were combined together and dried over anhydrous magnesium sulfate. Magnesium sulfate was filtered out and the solvent was evaporated under reduced pressure to obtain the intended benzyl ester of N,N-dibenzyl-L-phenylalanine (37.06 g) in a yield of 85%.

$^1$H-NMR(CDCl$_3$, 300 MHz) δ ppm: 2.99 (dd, J=8.2, 14.0 Hz, 1H), 3.14 (dd, J=14.0, 7.4 Hz, 1H), 3.53 (d, J=14.0 Hz, 1H), 3.71 (t, J=7.8 Hz, 1H), 3.92 (d, J=14.0 Hz, 1H), 5.11 (d, J=12.3 Hz, 1H), 5.23 (d, J=12.3 Hz, 1H), 6.95–7.40 (m, 20H) Mass spectrum m/e: 436 (MH+)

Example 12

A Process for Producing (3S)-1,1-dichloro-3-dibenzylamino-4-phenyl-2-butanone

Dehydrated tetrahydrofuran (15 ml) was cooled to −78° C. 1.53 M solution (6.5 ml) of n-butyllithium in hexane and then a solution of methylene chloride (0.8 ml) in dehydrated tetrahydrofuran (5 ml) were added thereto, and they were stirred for 10 minutes. A solution of benzyl ester (2.18 g) of N,N-dibenzyl-L-phenylalanine in dehydrated tetrahydrofuran (7 ml) was added to the obtained mixture, and they were stirred for 1 hour. 2 N hydrochloric acid (15 ml) and water (15 ml) were added to the reaction mixture to terminate the reaction. The temperature was elevated to room temperature. After the addition of water followed by the extraction with ethyl acetate, the obtained solutions in ethyl acetate were combined together and dried over anhydrous magnesium sulfate. Magnesium sulfate was filtered out. The solvent was evaporated under reduced pressure to obtain the intended (3S)-1,1-dichloro-3-dibenzylamino-4-phenyl-2-butanone (2.04 g) in a yield of 99%.

$^1$H-NMR(CDCl$_3$, 300 MHz) δ ppm: 3.04 (dd, J=3.8, 13.5 Hz, 1H), 3.23 (dd, J=9.6, 13.5 Hz, 1H), 3.54 (d, J=13.3 Hz, 2H), 3.83 (d, J=13.3 Hz, 2H), 3.95 (dd, J=3.8, 9.6 Hz, 1H), 6.14 (d, 1H), 7.12–7.40 (m, 15H)

According to the present invention, α-amino-dihalogenated methyl ketone derivatives and β-amino-α-hydroxycarboxylic acid derivatives can be efficiently produced at a low cost from N-protected α-amino acid esters. Because the optical activity can be kept, the process of the present invention is particularly suitable for producing intermediates of medicines having structures derived from optically active amino acids.

What is claimed is:

1. A process for Producing an α-amino-dihalogenated methyl ketone of formula (3):

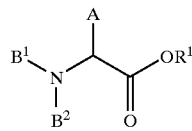

(3)

wherein either $B^3$ or $B^4$ is a carbamate-type protecting group and the other is a hydrogen atom;

A represents a hydrogen atom, an unsubstituted alkyl group having 1 to 10 carbon atoms, a substituted alkyl group having 1 to 10 carbon atoms, an unsubstituted aryl group having 6 to 15 carbon atoms, a substituted aryl group having 6 to 15 carbon atoms an unsubstituted aralkyl group having 7 to 20 carbon atoms, a substituted aralkyl group having 7 to 20 carbon atoms, or a group corresponding thereto which contains a hetero atom in the carbon skeleton; and $X^1$ and $X^2$ independently represent a chlorine atom or a bromine atom, which comprises reacting an N-protected α-amino acid ester of formula (1):

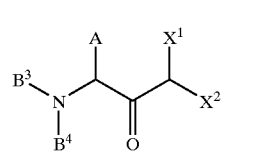

(1)

wherein either $B^1$ or $B^2$ is a carbamate-type protecting group and the other is a hydrogen atom, $R^1$ represents an unsubstituted lower alkyl group, substituted lower alkyl group, an unsubstituted aralkyl group, a substituted aralkyl group, a substituted aryl group or an unsubstituted aryl group, and A is as defined above

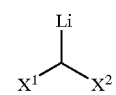

(2)

with a dihalomethyl lithium of formula (2) wherein $X^1$ and $X^2$ are as defined above.

2. The process according to claim 1, wherein both $X^1$ and $X^2$ are a chlorine atom or a bromine atom.

3. The process according to claim 1, wherein both $X^1$ and $X^2$ are a chlorine atom.

4. The process according to claim 1, wherein A is a benzyl group.

5. The process according to claim 1, wherein $R^1$ is an unsubstituted lower alkyl group, a substituted lower alkyl group, an unsubstituted aralkyl group, or a substituted aralkyl group and A is an unsubstituted alkyl group or a substituted alkyl group having 1 to 10 carbon atoms, an unsubstituted aryl group having 6 to 15 carbon atoms, a substituted aryl group having 6 to 15 carbon atoms, an unsubstituted aralkyl group having 7 to 20 carbon atoms, a substituted aralkyl group having 7 to 20 carbons, or a corresponding group which further contains a hetero atom in the carbon skeleton.

6. A process for producing a β-amino-α-hydroxycarboxylic acid of formula (4):

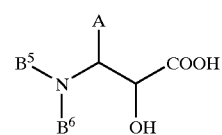

(4)

wherein $B^5$ and $B^6$ independently represent a hydrogen atom or an amino protecting group, or $B^5$ and $B^6$ together form an imine-type protecting group, and A represents a hydrogen atom, an unsubstituted alkyl group having 1 to 10 carbon atoms, a substituted alkyl group having 1 to 10 carbon atoms, an unsubstituted aryl group having 6 to 15 carbon atoms, a substituted aryl group having 6 to 15 carbon atoms, an unsubstituted aralkyl group having 7 to 20 carbon atoms, a substituted aralkyl group having 7 to 20 carbon atoms, or a group corresponding thereto which contains a hetero atom in the carbon skeleton, which comprises reacting an N-protected α-amino acid ester of formula (1):

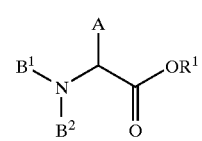

(1)

wherein $B^1$ and $B^2$ independently represent a hydrogen atom or an amino protecting group, or $B^1$ and $B^2$ together form an imine-type protecting group, wherein $B^1$ and $B^2$ are not a hydrogen atom at the same time, $R^1$ represent an unsubstituted lower alkyl group, a substituted lower alkyl group, an unsubstituted aralkyl group, a substituted aralkyl group, a substituted aryl group, or an unsubstituted aryl group, and A is as defined above with a dihalomethyl lithium of formula (2):

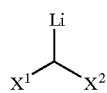
(2)

wherein $X^1$ and $X^2$ independently represent a chlorine atom or a bromine atom to form an α-amino-dihalogenated methyl ketone of formula (3):

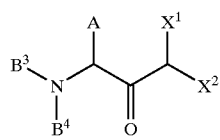
(3)

wherein $B^3$ and $B^4$ independently represent a hydrogen atom or an amino protecting group, or $B^3$ and $B^4$ together form an imine-type protecting group, and A, $X^1$ and $X^2$ are as defined above; and hydrolyzing in the presence of a base the α-amino-dihalogenated methyl ketone of formula (3).

7. The process according to claim 6, herein both $X^1$ and $X^2$ are a chlorine atom or a bromine atom.

8. The process according to claim 6, wherein both $X^1$ and $X^2$ are a chlorine atom.

9. The process according to claim 6, wherein either $B^1$ or $B^2$ is a carbamate-type protecting group and the other is a hydrogen atom, either $B^3$ or $B^4$ is a carbamate-type protecting group and the other is a hydrogen atom, and either $B^5$ or $B^6$ is a carbamate-type protecting group and the other is a hydrogen atom.

10. The process according to claim 6, wherein A is a benzyl group.

11. The process according to claim 6, wherein $R^1$ is an unsubstituted lower alkyl group, substituted lower alkyl group, an unsubstituted aralkyl group, or a substituted aralkyl group, and A is an unsubstituted alkyl group having 1 to 10 carbon atoms, a substituted alkyl group having 1 to 10 carbon atoms, an unsubstituted aryl group having 6 to 15 carbon atoms, a substituted aryl group having 6 to 15 carbon atoms, an unsubstituted aralkyl group having 7 to 20 carbon atoms, or a substituted aralkyl group having 7 to 20 carbon atoms, or a group corresponding thereto which contains a hetero atom in the carbon skeleton.

12. The process according to claim 1, wherein $X^1$ and $X^2$ are a bromine atom.

13. The process according to claim 12, wherein at least 2 molar equivalents to 3 molar equivalents of a dihalomethyl lithium per molar equivalent of the N-protected α-amino acid ester are employed.

14. The process according to claim 1, wherein one of $X^1$ and $X^2$ is a bromine atom and the other is a chlorine atom.

15. The process according to claim 14, wherein at least 2 molar equivalents to 3 molar equivalents of a dihalomethyl lithium per molar equivalent of the N-protected α-amino acid ester are employed.

16. The process according to claim 6, wherein $X^1$ and $X^2$ are a bromine atom.

17. The process according to claim 16, wherein at least 2 molar equivalents to 3 molar equivalents of a dihalomethyl lithium per molar equivalent of the N-protected α-amino acid ester are employed.

18. The process according to claim 6, wherein one of $X^1$ and $X^2$ is a bromine atom and the other is a chlorine atom.

19. The process according to claim 6, wherein at least 2 molar equivalents to 3 molar equivalents of a dihalomethyl lithium per molar equivalent of the N-protected α-amino acid ester are employed.

* * * * *

UNITED STATES PATENT AND TRADEMARK OFFICE
CERTIFICATE OF CORRECTION

PATENT NO. : 6,639,094 B2 Page 1 of 1
DATED : October 28, 2003
INVENTOR(S) : Onishi et al.

It is certified that error appears in the above-identified patent and that said Letters Patent is hereby corrected as shown below:

<u>Title page,</u>
Item [22], should read -- [22] Filed: Sep 12, 2001 --

Signed and Sealed this

Tenth Day of February, 2004

JON W. DUDAS
*Acting Director of the United States Patent and Trademark Office*